(12) United States Patent
von Wussow

(10) Patent No.: US 6,200,559 B1
(45) Date of Patent: Mar. 13, 2001

(54) USE OF ANTIBODIES AGAINST MXA OR MXB TO DETERMINE LEVELS OF TYPE I INTERFERONS IN VIVO

(76) Inventor: Peter von Wussow, Dammstrasse 30, Pattensen, D30982 (DE)

( * ) Notice: Subject to any disclaimer, the term of this patent is extended or adjusted under 35 U.S.C. 154(b) by 0 days.

(21) Appl. No.: 09/297,475

(22) PCT Filed: Oct. 31, 1997

(86) PCT No.: PCT/DE97/02536

§ 371 Date: Oct. 18, 1999

§ 102(e) Date: Oct. 18, 1999

(87) PCT Pub. No.: WO98/19160

PCT Pub. Date: May 7, 1998

(30) Foreign Application Priority Data

Oct. 31, 1996 (DE) ............................................... 196 45 010

(51) Int. Cl.[7] .................. C07K 16/18; G01N 33/68; A61K 38/21
(52) U.S. Cl. .................. 424/85.4; 424/85.5; 424/85.6; 424/143.1; 424/145.1; 530/388.2; 435/7.1; 435/7.8; 435/7.92
(58) Field of Search .................. 424/85.4, 85.5, 424/85.6, 143.1, 145.1; 530/388.2; 435/7.1, 7.8, 7.92

(56) References Cited

U.S. PATENT DOCUMENTS 5,863,742 * 1/1999 Oh et al. ............................. 435/7.21
5,869,264 * 2/1999 Horisberger et al. ................. 435/7.1

OTHER PUBLICATIONS

"cDNA Structures and Regulation of Two Interferon–Induced Human Mx Proteins," *Molecular and Cellular Biology*, Nov. 1989, vol. 9–11, pp. 5062–5072.

"Human MXB protein, an interferon–α–inducible GTPase, contains a nuclear tarteting signal and is localized in the heterochromatin region beneath the nuclear envelope," *Chemical Abstracts*, vol. 125, No. 19, 1996, p. 722.

"Strong Transient Expression of the Type I Interferon–induced MxA Protein in Hepatitis A but not in Acute Hepatitis B and C," *Hepatology*, vol. 19(4), 1994, pp. 857–865.

* cited by examiner

*Primary Examiner*—David L. Fitzgerald
(74) *Attorney, Agent, or Firm*—Locke Reynolds LLP

(57) ABSTRACT

The invention provides methods of indirectly measuring the level of type I interferons in vivo utilizing antibodies directed against MxA and/or MxB. The methods find application in conjunction with therapies directed to raising or lowering the levels of interferons in patients. Also provided are new monoclonal antibodies that recognize specific human Mx protein(s).

15 Claims, 12 Drawing Sheets

Mx – Level in HIV-pos. Patients

Figure 1:
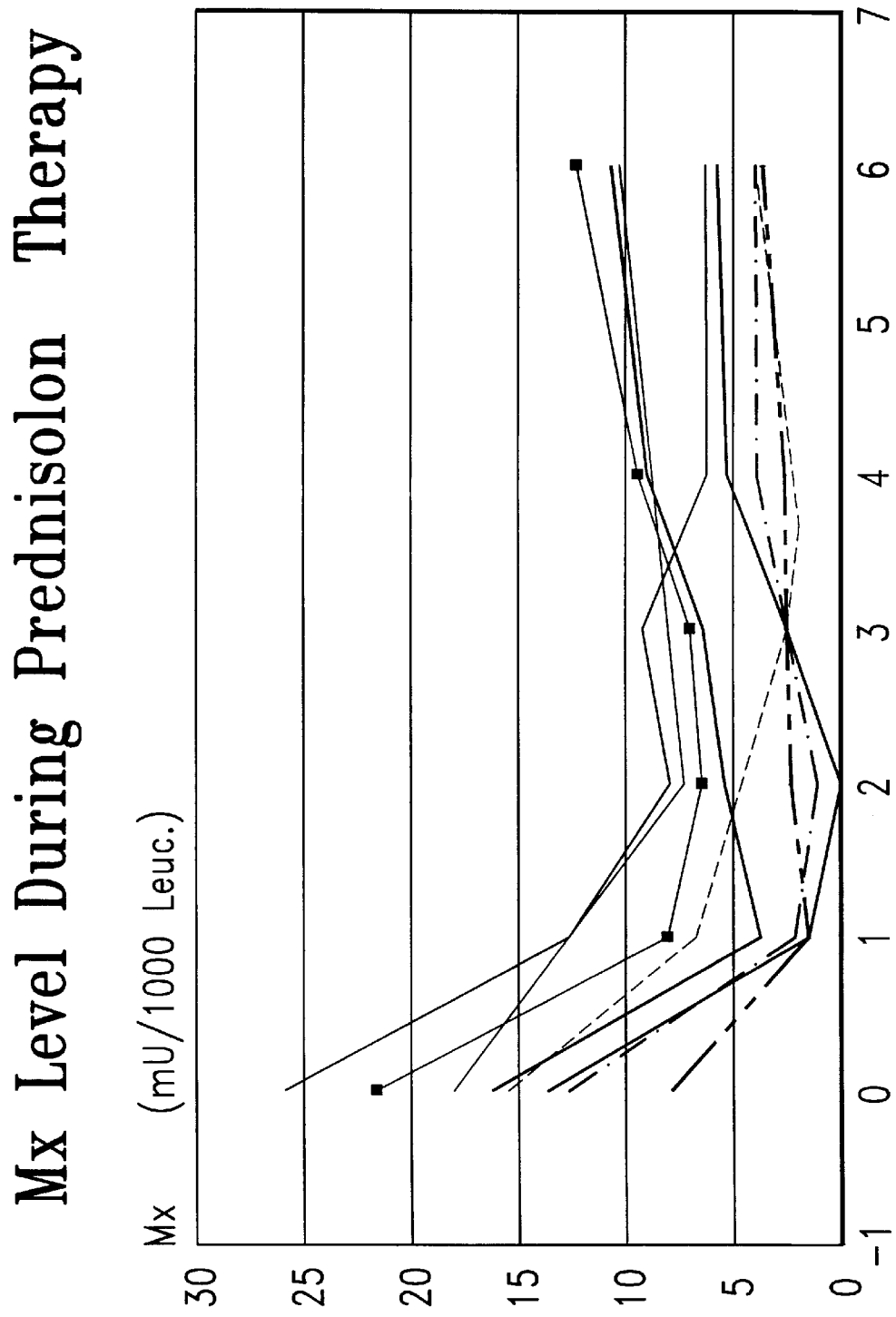

CDC-Classification
n=74

| CDC Class / | Controls | CDC I | CDC II | CDC III |
|---|---|---|---|---|
| Mx mU/1000 leucocytes | 1,24 ±0,57 | 5,36 ±2,69 | 10,92 ±12,69 | 58,42 ±46,41 |

Controls vs CDC I: $p<0{,}0001$
CDC I vs CDC II: $p=0{,}02$
CDC II vs CDC III: $p<0{,}0001$

Fig. 3

USE OF ANTIBODIES AGAINST MXA OR MXB TO DETERMINE LEVELS OF TYPE I INTERFERONS IN VIVO

The invention concerns antibodies and a procedure for indirect detection of interferon production by means of antibodies against Mx proteins, especially MxA protein and/or MxB protein, as well as the utilization of interferon for increasing a lowered Mx protein level and the utilization of anti-interferon medications for lowering an elevated MxA and/or MxB level.

Interferons, especially interferon $\alpha$, $\beta$ and $\omega$, are a class of naturally occurring proteins, which are known to have a favorable effect in viral infections and in the prevention of tumor growth. Furthermore, interferons stimulate the activity of natural killer cells and modulate the activity of macrophages, B- and T-cells.

Interferons are therefore important factors of the immune system, yet, too high levels of interferon have unfavorable side effects, as for example bone marrow toxicity, CNS-toxicity or fever.

A number of proteins are induced by interferons that take part in the antiviral, anti-prolific and immune-modulatory activity that is ascribed to interferons. Two of these interferon-induced proteins are the MxA and the MxB protein (Markus Aebi et al., Mol. Cell. Biol. 1989, 9: 5062–5072).

Because one can make an assesment, by means of measurement of the endogenous interferon production, of the activity of the immune system, and since with various illnesses one has to know whether a too high or too low interferon production is taking place, it remains the task of the present invention to provide a simple procedure for measurement of the interferon production. Further it remains the task of the present invention to provide an option to adjust a too high or a too low measured interferon production to normal levels. Furthermore, it is a task of the invention to provide the corresponding antibodies.

The inventors have found that type I interferon production in vivo can be measured through the utilization of antibodies against Mx proteins, particularly MxA and/or MxB protein. There exists a correlation between the production of interferons in a patient and the expression of interferon-induced proteins MxA and/or MxB, i.e., at a too high interferon production in the body the concentration of MxA and/or MxB is also elevated, and correspondingly with a too low production of interferon the concentration is lowered.

According to the invention, the determination of MxA and/or MxB contents is done immunologically by the utilization of antibodies against these proteins. According to the invention, it is possible to use polyclonal or monoclonal antibodies, correspondingly fragments or conjugates thereof.

For the production of antibodies one first obtains MxA and/or MxB protein. This is done preferably by cultivating murine or human cells, e.g. lymphocytes, macrophages, monocytes or lymphoblastoid cells in a common growth medium (i.e. RPMI 1640 medium), possibly enriched with vitamins and/or hormones. At the end of the exponential growth-phase, the cells are incubated with natural or recombinant interferon, in concentration of $5 \times 10^4$ to $10^8$ cells/ml and 3,000 to 12,000 international units of interferon/ml. Following, the cells are harvested and lysed according to standard methods. The protein, respectively the proteins are purified, i.e. by means of column chromatography, HPLC or electrophoresis, and are used as antigenes for the generation of antibodies. Also, a recombinant production is possible.

Polyclonal antibodies are obtained by standard methods of injecting the purified MxA and/or MxB protein into mice or rabbits, and isolating the antibodies from the blood serum of the immunized animal, i.e., by affinity chromatography.

Monoclonal antibodies are obtained by means of standard methods. Preferably, an Mx negative mouse is injected with purified Mx1 and/or MxB protein. Antibody-producing cells (i.e. from the spleen) of the immunized animal are extracted and fused with myeloma cells, whereby the fused cells are cloned afterwards. The thereby obtained hybriduma cells are cultivated in vitro (i.e. in Dulbecco's Modified Eagle Medium, or RPMI 1640 Medium), and the monoclonal antibodies are obtained from the culture supernatant. Suitable methods for that are known to specialists, like precipitation with ammonium sulfate, followed by purification of the immune globulins through standard chromatographic procedures.

The inventors have deposited monoclonal antibodies against MxB protein at the DSM, Braunschweig, Mascheroder Weg 1b, D-38124 Germany on Jun. 16, 1997, listed as number DSM-ACC 2309 (internal label 8-271) and as number DSM-ACC 2309 (internal label 7-88). Monoclonal antibodies against MxA+MxB protein were deposited under the number DSM-ACC 2289 (internal label 2-95) and DSM-ACC 2290 (internal label 5-237) on Dec. 6, 1996.

Objects of the invention are also the corresponding antibodies.

Fragments of the Antibodies, i.e. Fab, Fab' or F(ab')$_2$ fragments can be generated if the above purified antibodies are digested with enzymes (i.e. pepsin or papain), or the disulfide bonds are reduced chemically.

Also, conjugates of the antibodies or fragments thereof can be generated, i.e. if the antibodies or fragments thereof are coupled with glutaraldehyd, biotin or avidin.

According to the invention, the term antibody should be understood in a way that it comprises either monoclonal or polyclonal antibodies as well as fragments or conjugates thereof.

The inventors have uncovered the following new contexts:

1) The Mx proteins indicate activity of illness with systemic *Lupus erythemotodes* (SLE) and with mixed collagenosis;
2) The Mx-proteins indicate the progress of the HIV infection and are hereby a prognostic marker for the survival of the patients;
3) Through staining of histological sections Mx antibodies indicate SLE activity in kidney sections;
4) Through staining of histological sections of transplant tissue Mx antibodies indicate rejection:
5) In in vitro cultures of human HIV infected mononuclear cells high Mx levels are measured. In the presence of anti-retroviral active medications the Mx-levels decrease.

All applications have in common, that killer cells, especially T cell-mediated attacks on human cells, stimulate the latter to express Mx proteins.

The inventors have furthermore found that AIDS patients produce phase-dependent increasing interferon. These patients produce partially more interferon than patients who are on interferon-$\alpha$ medication. Patients on therapeutic interferon-$\alpha$ medication were often suffering of side effects like bone marrow toxicity, CNS toxicity or fever. AIDS-patients who produce too much interferon also have exactly these symptoms.

Similarly is the situation with patients who suffer an autoimmune disease or who are receiving a steroid therapy.

Already a short-time administration of steroids, i.e. of cortinsones (i.e. prednisolon), is sufficient to decrease the Mx content below a certain level.

The inventors now found that the increase or the decrease of the endogenous interferon production (interferon type I) can easily be determined by detecting elevated or lowered MxA and/or MxB protein levels in cell-containing body fluids (i.e. blood, urine, cerebrospinal fluid ). This is accomplished by employing suitable immunological detection systems, i.e. ELISA or RIA, and using antibodies or fragments or conjugates thereof against MxA and/or MxB protein, to determine the content of MxA and/or MxB protein. From an elevated or lowered content of MxA protein and/or MxB protein in the examined body fluid of the patient one can infer an elevated or a lowered interferon production of the patient, respectively. It was found that an Mx concentration of 0.5 to 2.0 mU/1000 leukocytes can be regarded as normal and reflects a normal production of interferon in the patient.

If, according to the invention, elevated MxA or MxB concentrations are detected, anti-interferon medications (i.e. steroids, anti-interferon antibodies) are administered in a suitable amount, so that the above mentioned normal concentrations of MxA and/or MxB are reached. Such a treatment has been proven to be very advantageous to avoid or remediate the symptoms that occur with AIDS. According to this invention, the Mx measurement allows the determination of the type I interferon production in patients with an HIV infection. Surprisingly, the investigations of the inventors showed that all untreated HIV-infected patients independently of their phase have an elevated Mx level and that the Mx level significantly increases with progression of the illness. Blood mononuclear cells of HIV-infected people incubated in vitro with anti-retroviral effective substances express essentially less Mx. Therefore, anti-virally effective substances can be identified this way. It is known that exogenously administered IFN-α, if given for longer period of time and especially in high dosages, may cause, in humans, leucopenia and polyneuropathic/depressive symptoms as well as lowered CD4 cell counts. Exactly these symptoms are also found, if high Mx concentrations occur in HIV infected patients. Surprisingly, leucopenia and polyneuropathic/depressive symptoms correlate with the level of Mx proteins and therefore with the level of the endogenously produced amount of IFN in AIDS patients. Therefore, one has to make sure that less active interferon is present in AIDS patients. Likewise, for example, an anti-IFN-α antibody therapy, or an anti-IFN-α, β receptor antibody therapy is carried out which blocks the endogenous IFN and reduces, respectively abolishes the symptoms of leukopenia and the polyneuropathic/depressive symptoms. This therapy must be executed for a longer term (ca. 4 weeks to 6 months). In this context one is referred to FIGS. 3 to 10.

Reversibly, if too low Mx concentration are detected, interferon (Type I) can administered to reach the above mentioned normal values. By that, for example, some of the known side effects of the steroid therapy can be avoided or significantly remediated. A steroid therapy with daily dosages above 20 mg prednisolon leads to a susceptibility to infections, especially to viruses, since the endogenous IFN production is decreased and therefore the Mx level decreases. Also steroids in middle to high dosages reduce the Mx level from 2 mU to 0.2 mU per 1000 leukocytes. Since elevated Mx levels are associated with protection towards viruses, it is to expect that a lowering of the endogenous IFN production is connected to an elevated susceptibility to viruses. To counteract this trend, a low dosed IFN therapy is recommendable, since it causes, even in the presence of steroids, an increase of Mx concentration in the peripheral blood. The inventors have determined that a low-dosed IFN therapy (i.g. 200,000 to 1,000,000 U/day IFN-α) can abolish the susceptibility to infections, caused by steroid administration. In this context, one is referred to FIGS. 1 and 2.

The inventors furthermore have carried out Mx measurements to control the activity of patients with auto-immune diseases and transplants. Patients with systemic *Lupus erythomatodes* (SLE) and those with collagenoses (MCTD) are predominantly Mx positive, as far as they show an activity of illness and are not receiving steroid medications. Also, patients with subcutaneous *Lupus erythomatodes* have Mx positive blood. Patients with discoid Lupus have normal Mx concentrations in the blood, but elevated Mx levels of the skin.

Patients with SLE and those with MCTD have normal Mx values in the inactive stage of their illness. Patients in the active stage have elevated Mx values and therefore an elevated endogenous interferon production. Under steroid therapy Mx values decrease again, so that even interferon administrations could be indicated. The inventors have determined, anyway, a close correlation of the Mx values of peripheral blood and the activity of the illness.

Mx stains show, that granulocytes, lymphocytes and monocytes, as well as part of the placenta can become MxA positive. Normal skin is Mx negative, patients with a type I interferon therapy have intensive Mx positive keratinocytes, muscle cells, sweat and sebaceous gland cells. Additionally, it was determined that transplanted tissue (heart) is Mx-positive in the rejection reaction and therefore indicates an elevated interferon production, which by means of appropriate anti-interferon medication can be lowered.

The invention is now further described with reference to the figures which show:

FIG. 1: Mx level during prednisolon therapy of collagenoses patients.

Figure 2:
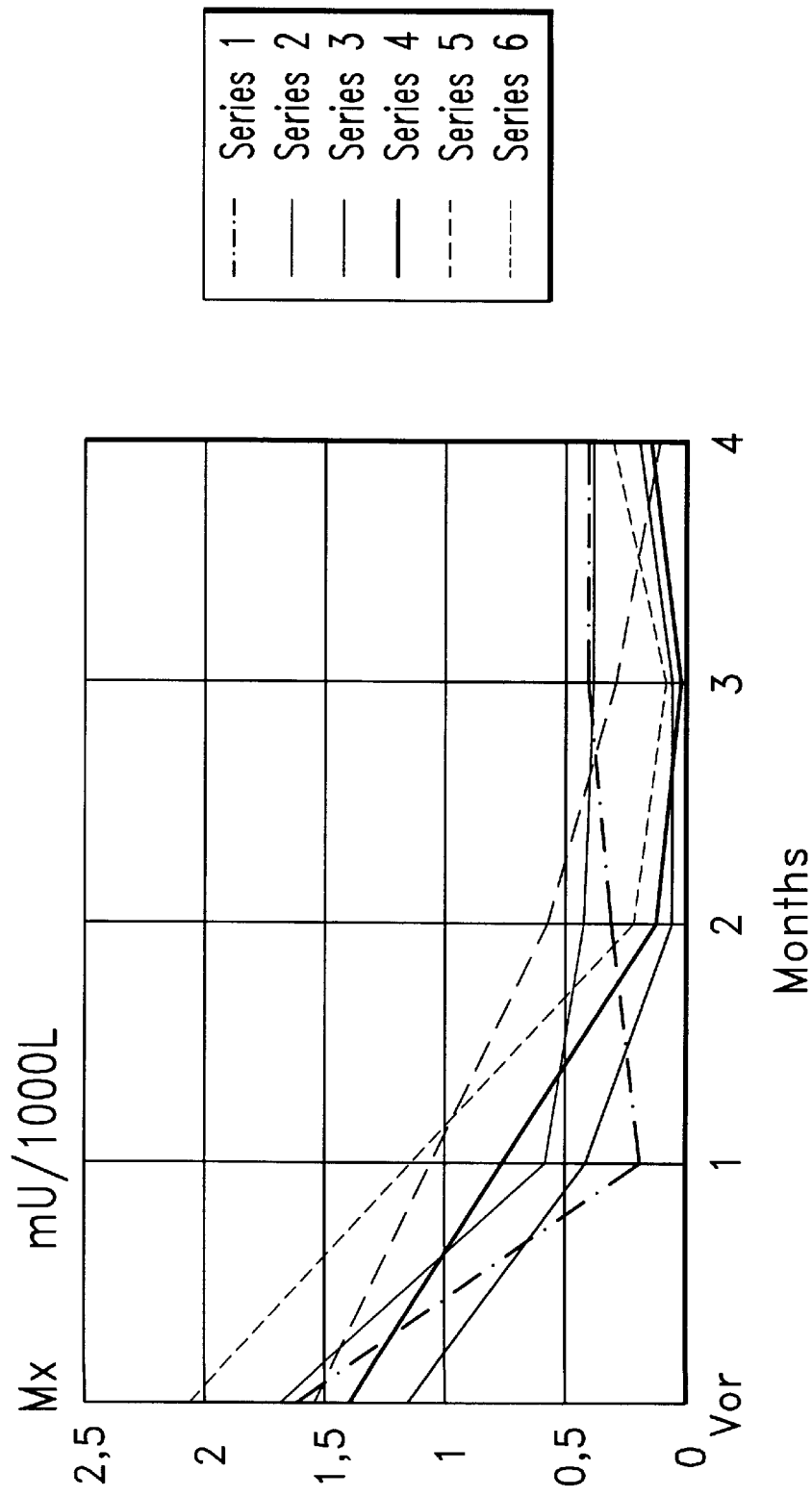

FIG. 2: Mx level before and after therapy with prednisolon on tumor patients.

FIG. 3: Mx level in HIV-positive patients.

Figure 4:
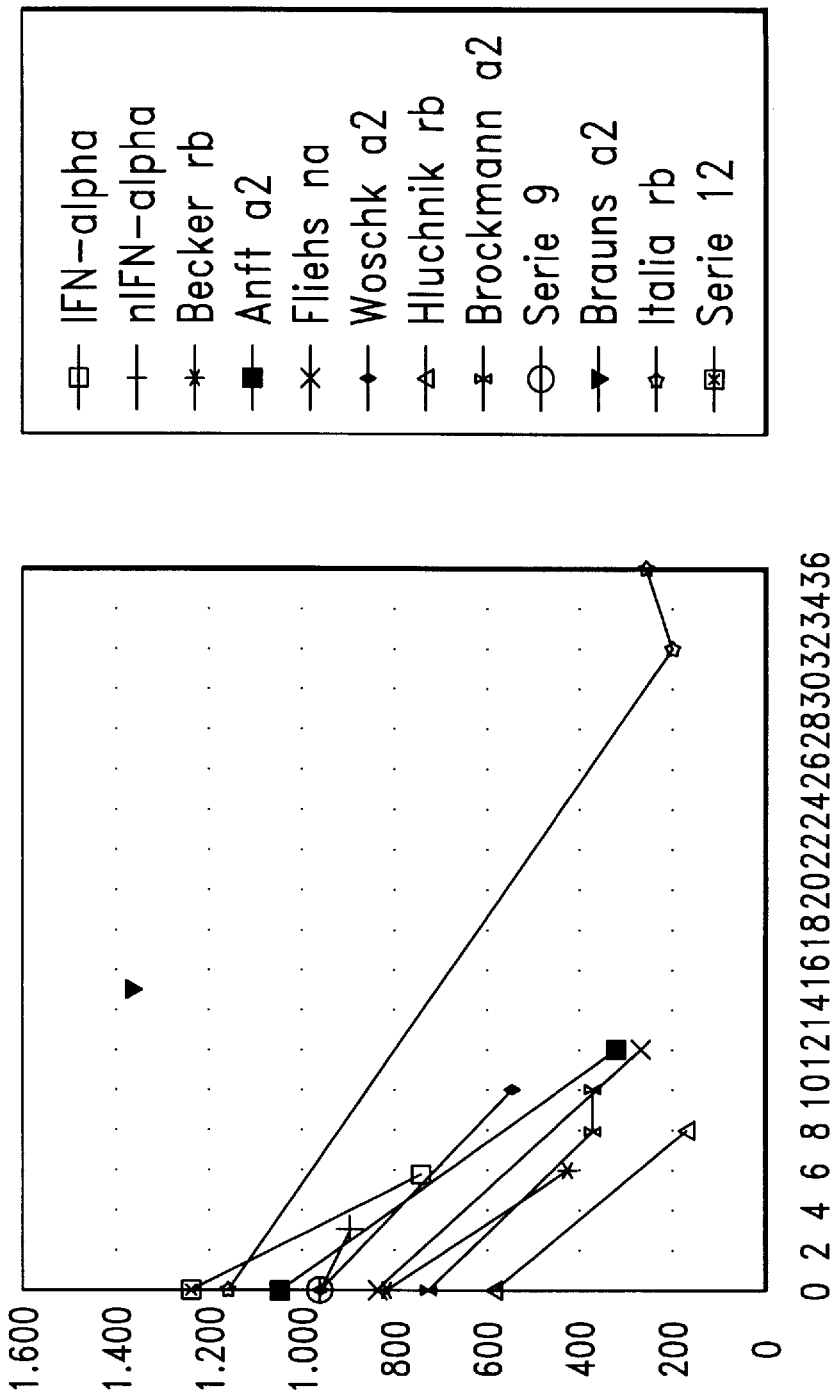

FIG. 4: CD4 cells during IFN therapy.

Figure 5:
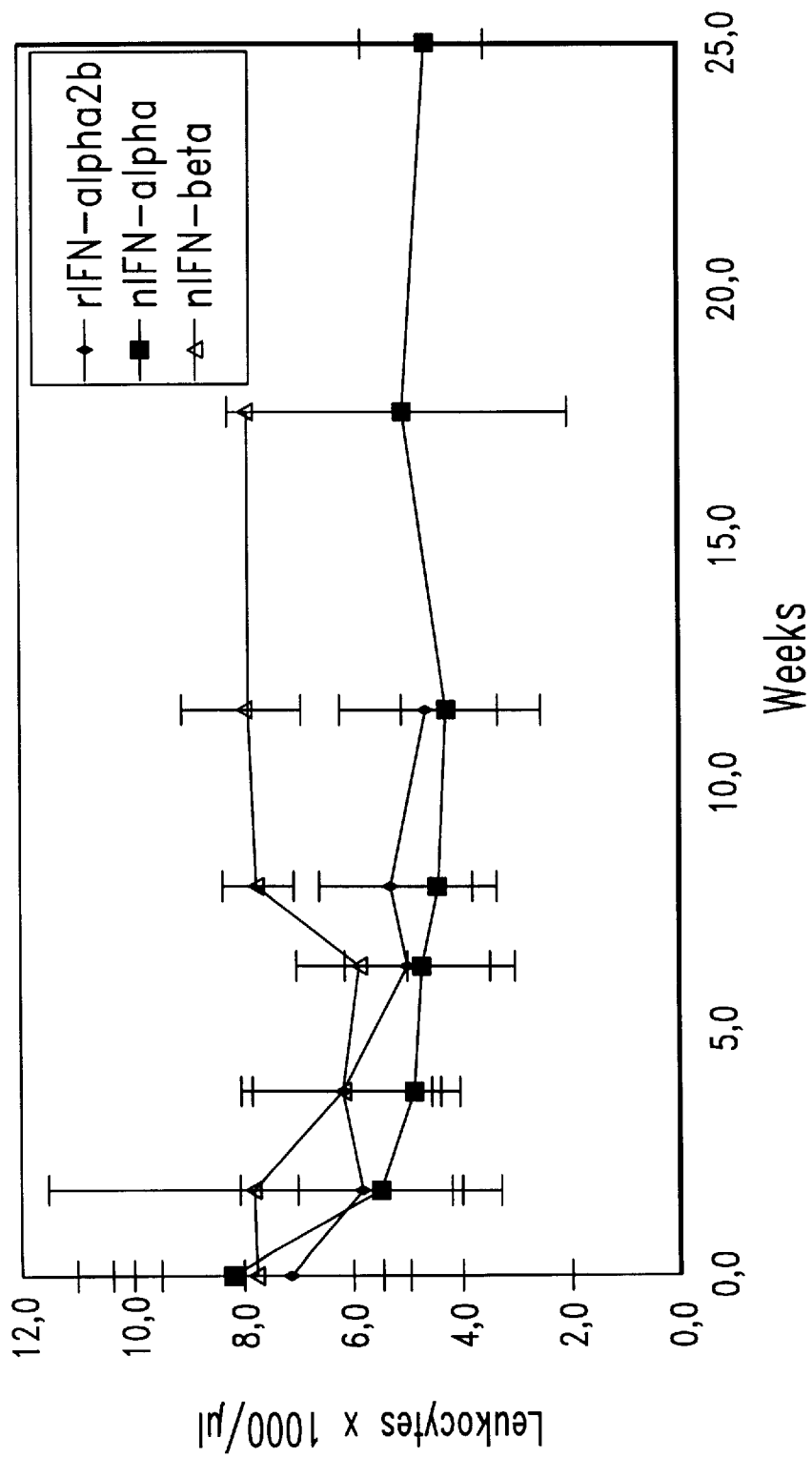

FIG. 5: Leukocytes changes under the IFN therapy.

Figure 6:
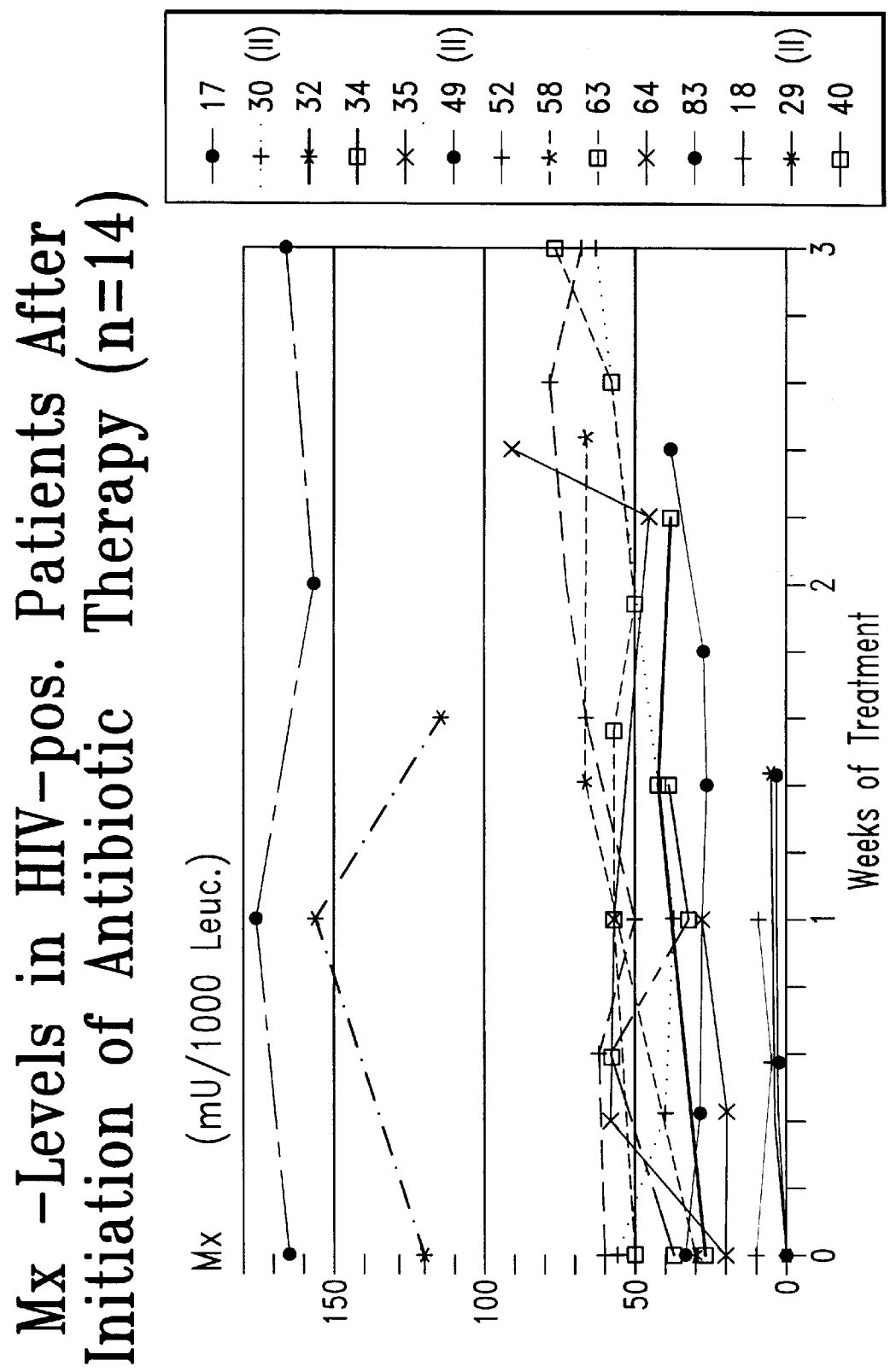
Figure 7:
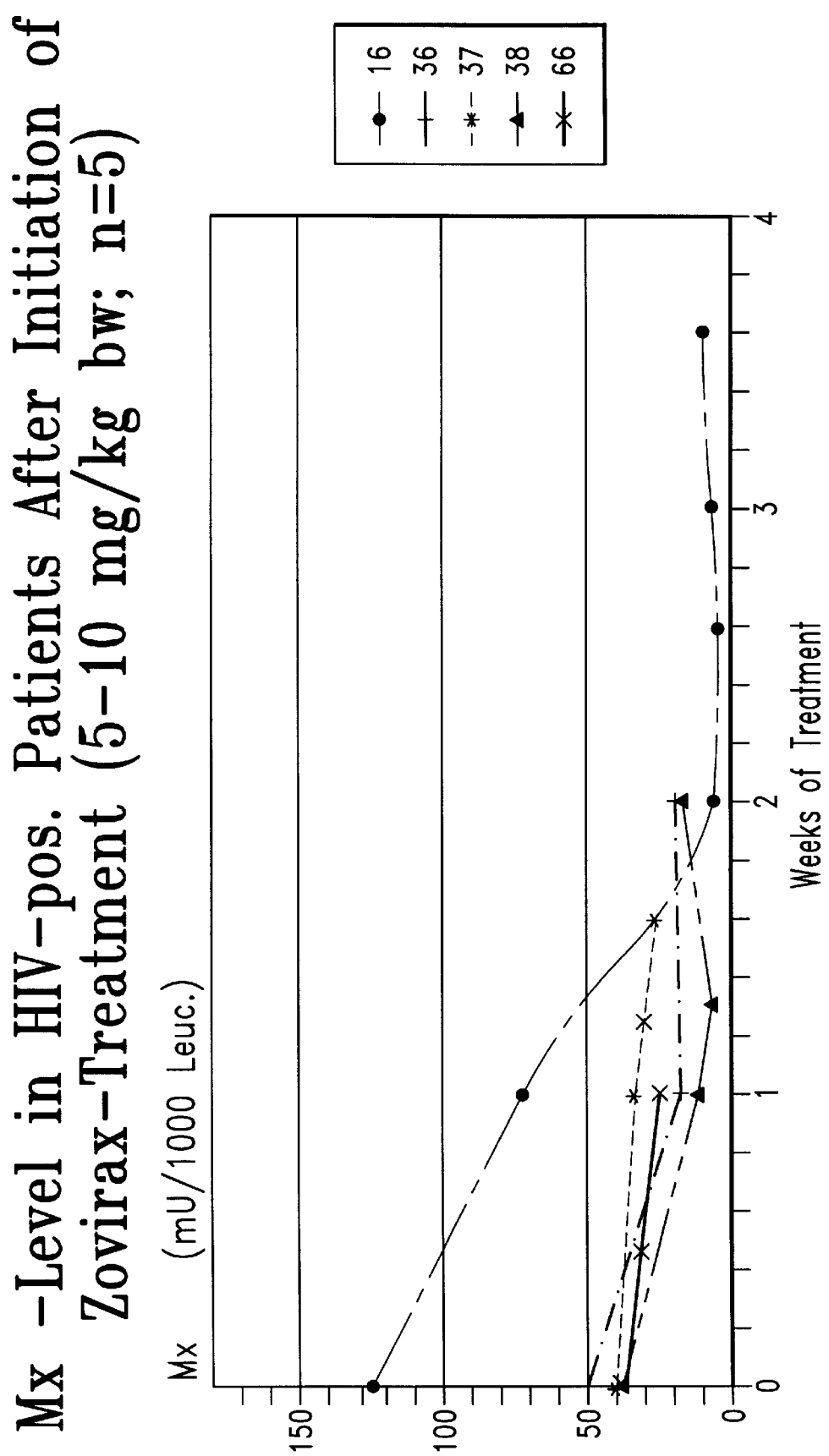

FIG. 6: Mx level in HIV-positive patients after initiation of antibiotic therapy FIG. 7: Mx level in HIV-positive patients after initiation of Zovirax treatment.

Figure 8:
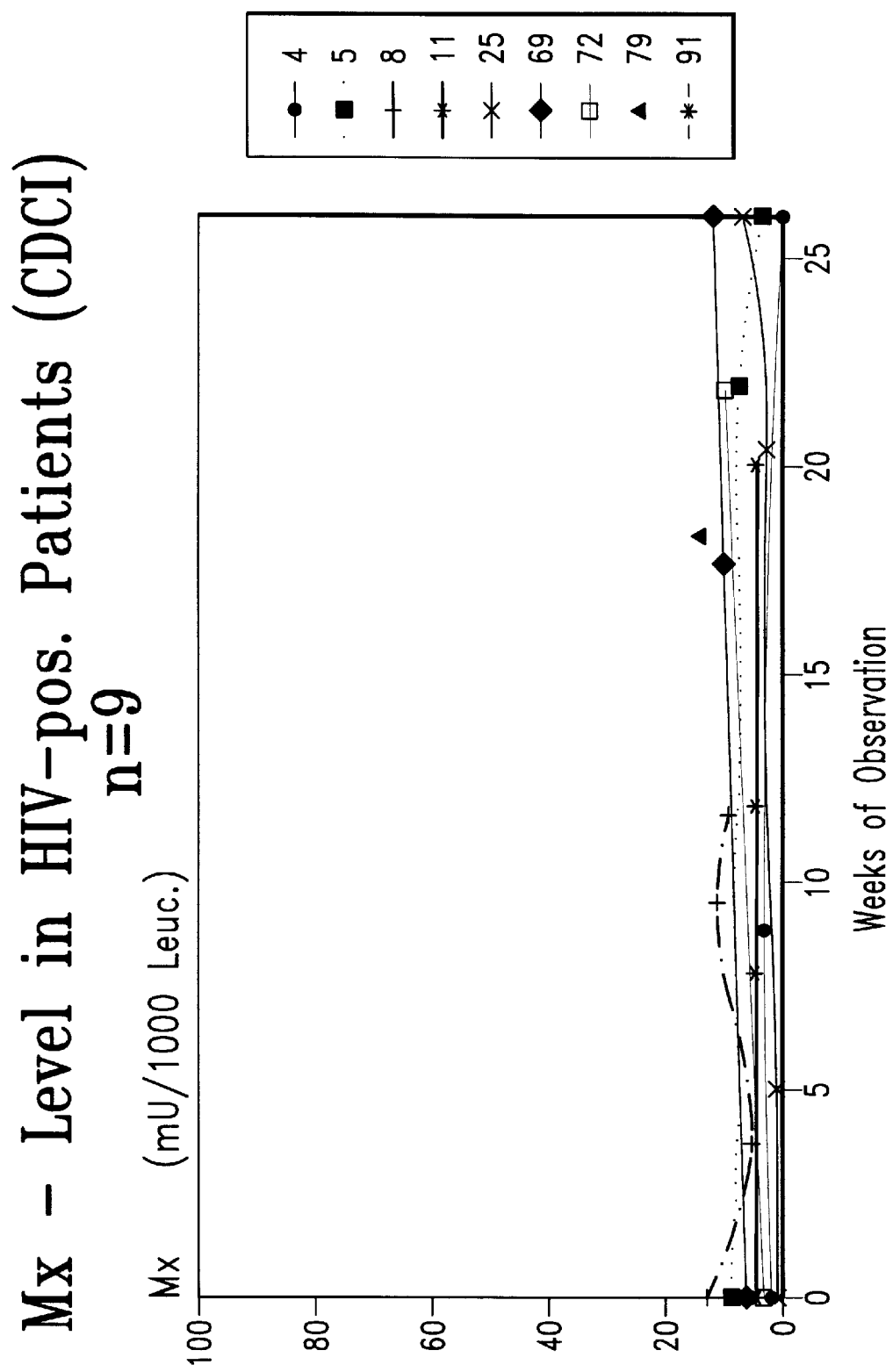

FIG. 8: Mx level in HIV-positive patients (CDC I)

Figure 9:
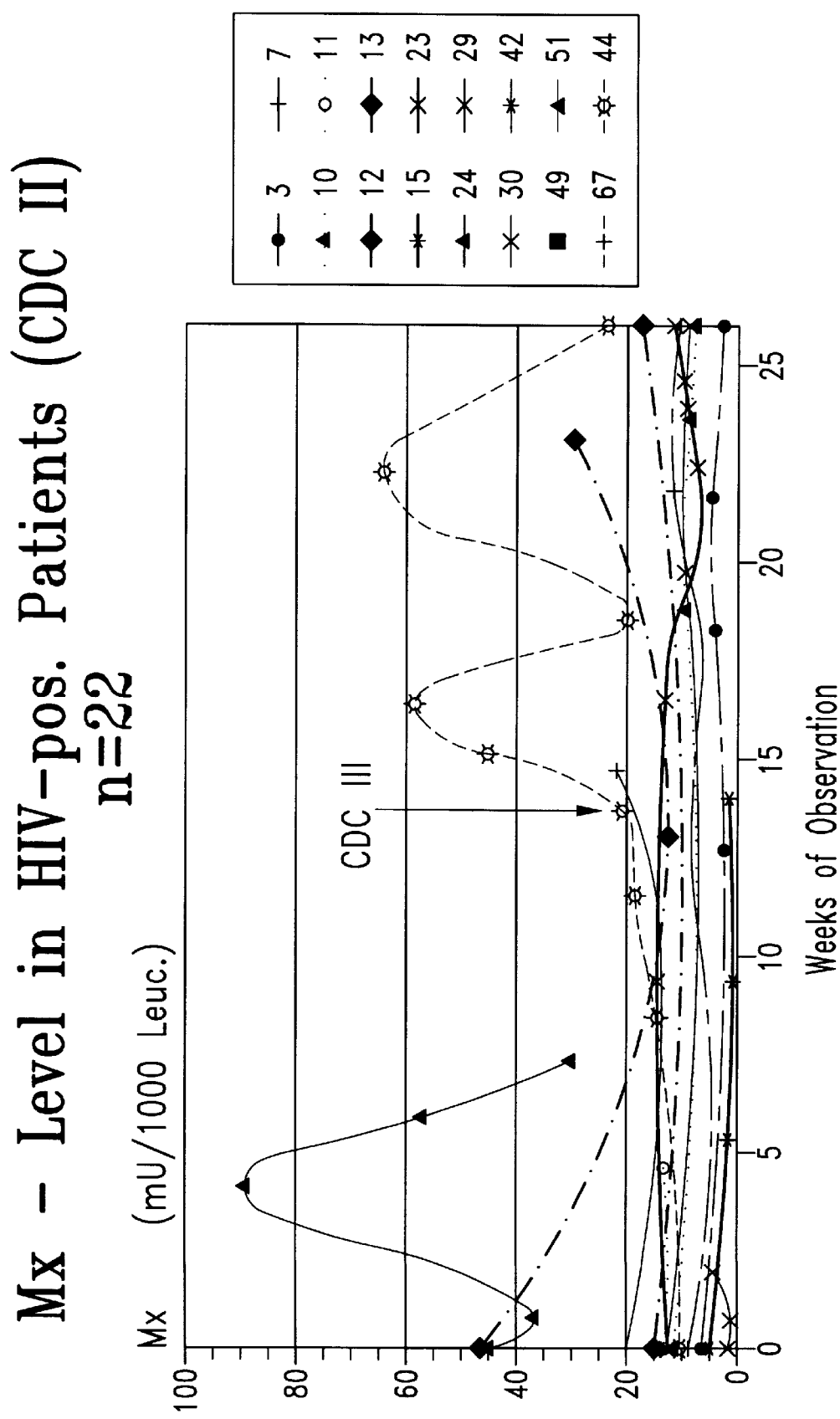

FIG. 9: Mx level in HIV-positive patients (CDC II)

Figure 10:
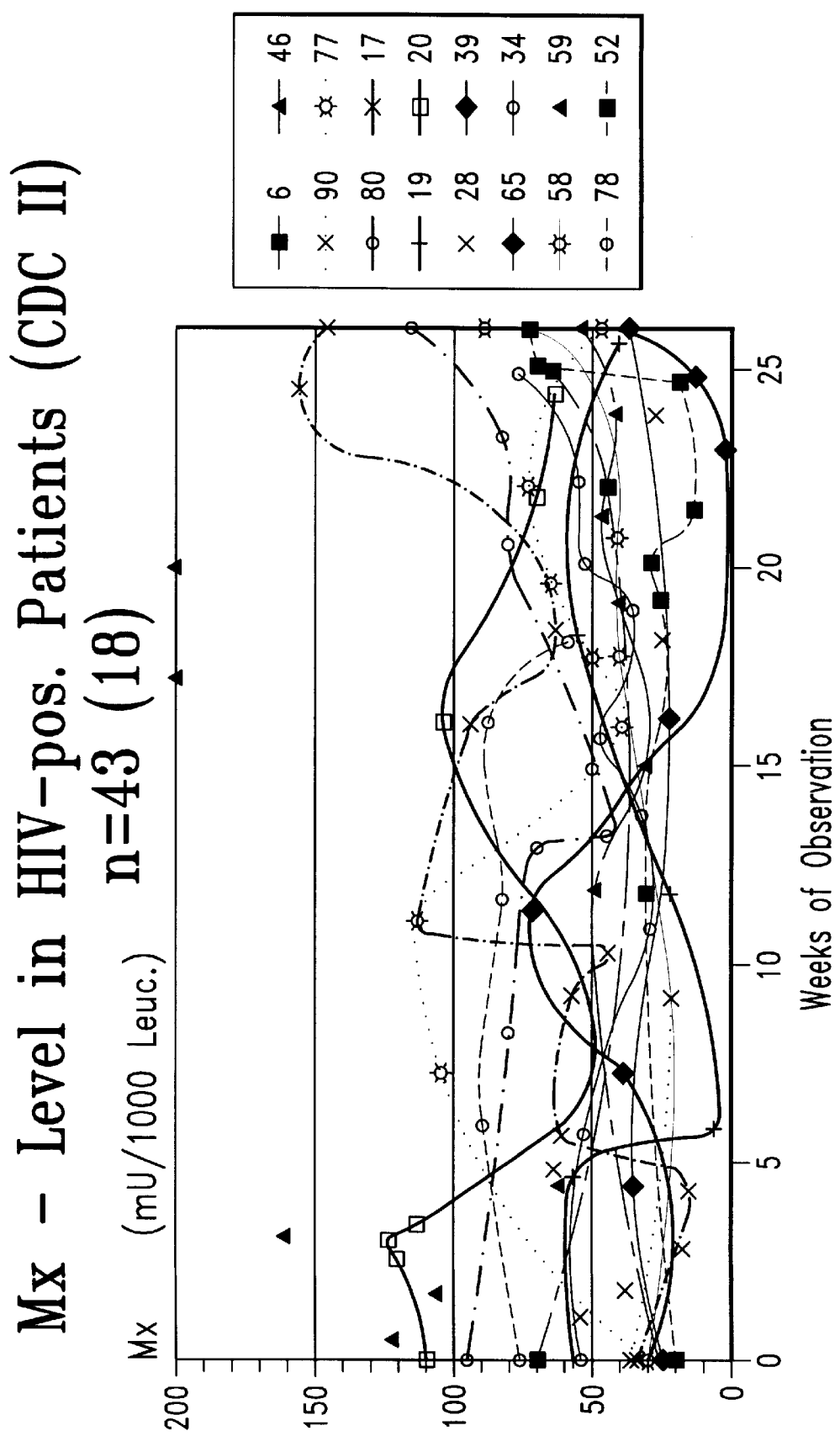

FIG. 10: Mx level in HIV-positive patients (CDC III)

Figure 11:
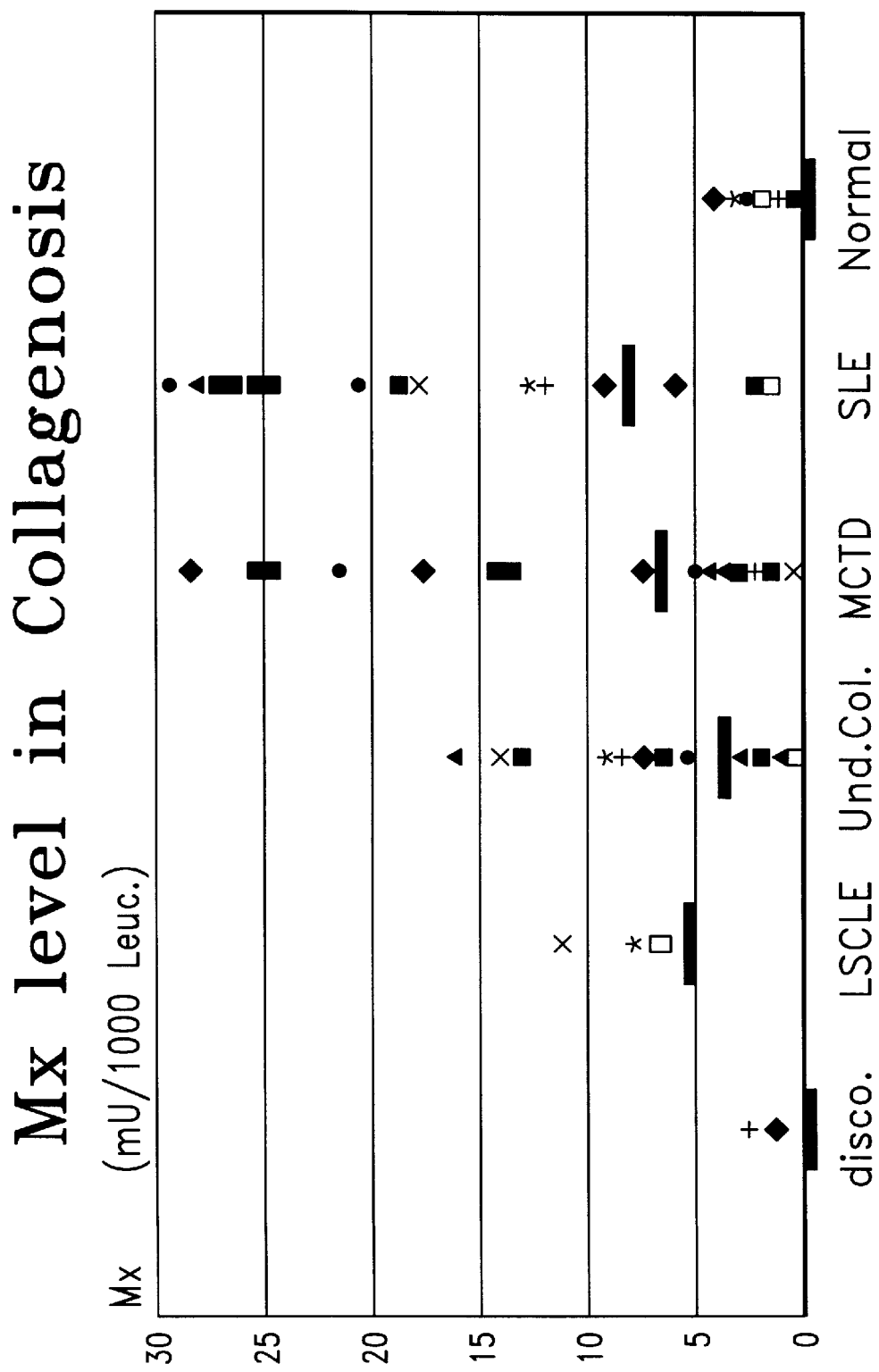

FIG. 11: Mx level in collagenoses

Figure 12:
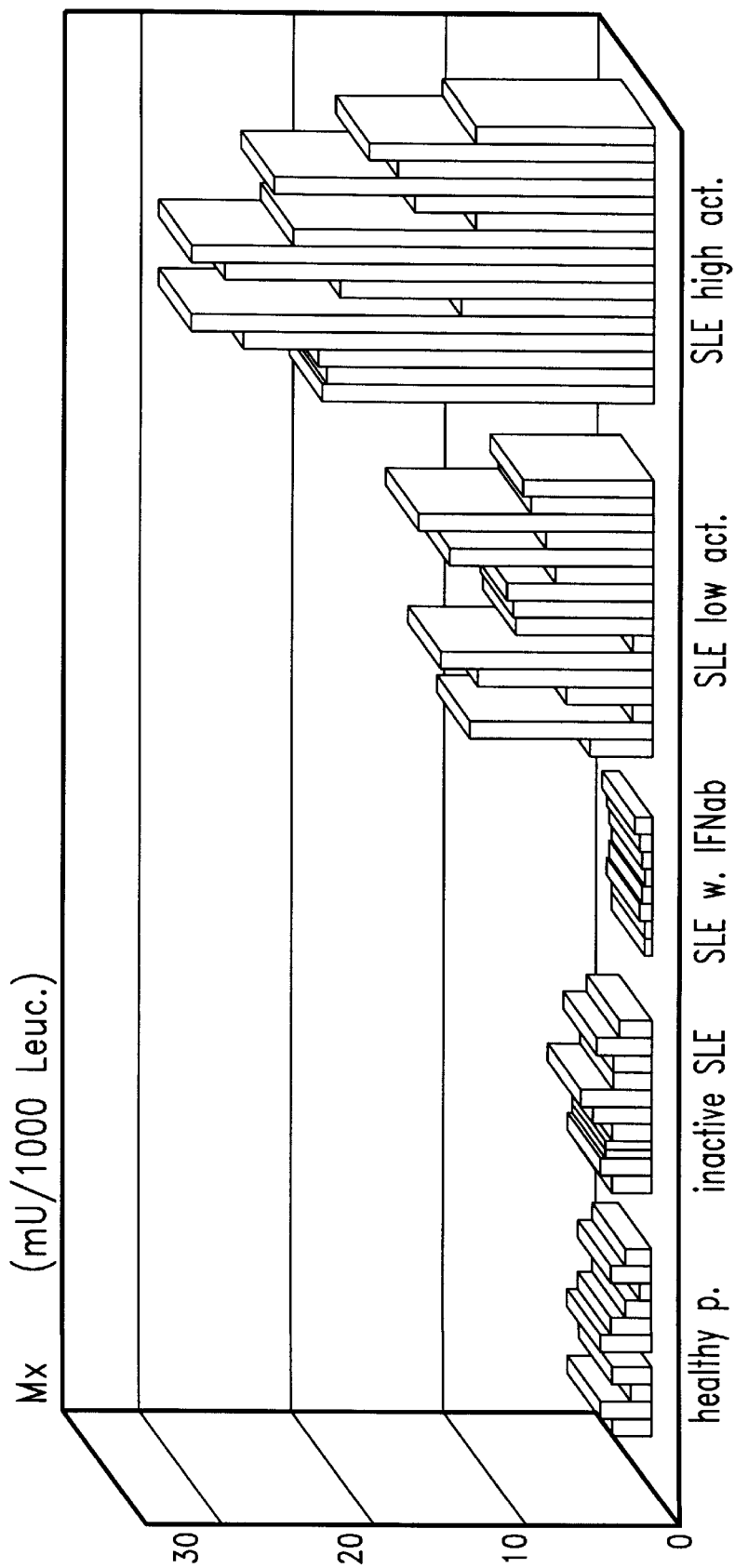

FIG. 12: Blood MxA level in SLE patients

Further, the invention is described according to following examples:

EXAMPLE 1

Isolation of a Monoclonal Antibody Targeted Against MxA and/or MxB

Female Balb/c mice are injected subcutaneously with 10 μg of recombinant MxB. On day 27 the mice receive recombinant MxA, 10 μg as well. On day 51, the mice receive again 10 μg MxB intravenously. On day 55 the mice are killed, the spleen extracted and these spleen cells are fused with SP2-O myeloma cell line (standard procedure). Supernatants of the hybridoma cultures are tested in a screening procedure. Qualified positive cultures become subject to a limiting-dilution procedure and that way hybridoma clones are obtained.

The clones 2308 and 2309/2289 and 2290 are propagated in the culture and are placed into a techno mouse. The thus isolated antibody-containing supernatants are purified by means of protein A-chromatography.

96-well microtiter plates are coated either with MxA or MxB in a concentration of 5 µg/ml for 16 hours at 4° C. Following is a blocking with bovine serum albumin. After washing of the plates, the hybridoma supernatants are incubated for 24 hours at room temperature in this plate. After repeated washing, alkaline phosphate-coupled sheep anti-mouse IgG-antibodies are added to the plate for 1 hour, and repeatedly washed. For the development of the dye reaction p-nitrophenylphosphatase is used. Clones are selected which recognize either MxA as well as MxB, or only MxB.

EXAMPLE 2

MxA and MxB-Specific ELISA

A monoclonal antibody is biotinylated according to a standard procedure. Following an ELISA is set up with both antibodies.

20 µl of lysed citrate blood or of a cell suspension are placed on 96-well microtiter plates for 16 hours at room temperature, which were previously coated with a non-biotinylated monoclonal antibody (5 µg/ml). After extensive washing the biotinylated antibody is added for 2 hours. After repeated washing an avidin-alkalic phosphatase-conjugate is added. After another wash step the intensity of a dye reaction is measured at 405 nm after addition of p-nitrophenylenphosphate. This ELISA detects, in dependence of the used antibody, MxA and MxB, or only MxB only roughly equally well. The Mx concentration of the blood is indicated in mU/1000 leukocytes.

What is claimed is:

1. An antibody selected from the group consisting of:
   monoclonal antibody 2-95 (DSM 2289) or a fragment or conjugate thereof that specifically binds to MxA and MxB;
   monoclonal antibody 5-237 (DSM 2290) or a fragment or conjugate thereof that specifically binds to MxA and MxB;
   monoclonal antibody 8-271 (DSM 2308) or a fragment or conjugate thereof that specifically binds to MxB; and
   monoclonal antibody 7-88 (DSM 2309) or a fragment or conjugate thereof that specifically binds to MxB.

2. A method of measuring Mx proteins in a biological sample comprising
   (a) contacting the sample with an antibody according to claim 1, and
   (b) detecting the immune complex(es) formed between the antibody and the Mx proteins present in the sample.

3. A method according to claim 2 wherein the level of Mx proteins in the sample is quantitated.

4. A method according to claim 3 wherein the level of Mx proteins is quantitated by ELISA or radioimmunoassay.

5. A method according to claim 3 wherein the biological sample is blood, urine, or cerebrospinal fluid.

6. A method according to claim 3, further comprising the step of comparing the measured level of Mx proteins to a standard range, wherein the level of Mx proteins relative to the standard range is used as a diagnostic indicator for the activity of interferons in vivo.

7. A method according to claim 6 wherein the standard range is 0.5 to 2.0 mU per 1000 leukocytes.

8. A method for treating a patient, comprising the steps of
   (a) obtaining a biological sample from the patient,
   (b) determining the level of Mx proteins in the sample relative to a standard range according to the method of claim 6, and
   (c) administering an agent which increases the activity of interferons in vivo to the patient.

9. A method according to claim 8, wherein the amount of the agent administered is effective to achieve a level of Mx proteins in the patient within said standard range.

10. A method according to claim 8, wherein the agent comprises one or more type I interferons of natural or recombinant origin.

11. A method according to claim 10 wherein the one or more type I interferons are selected from the group consisting of interferon-α, interferon-β, and interferon-ω.

12. A method for treating a patient, comprising the steps of
   (a) obtaining a biological sample from the patient,
   (b) determining the level of Mx proteins in the sample relative to a standard range according to the method of claim 6, and
   (c) administering an agent which decreases the activity of interferons in vivo to the patient.

13. A method according to claim 12, wherein the amount of the agent administered is effective to achieve a level of Mx proteins in the patient within said standard range.

14. A method according to claim 12 wherein the agent comprises an inhibitory antibody directed against interferon-α or the interferon-α/β receptor.

15. A method for assessing the effectiveness of an antiretroviral substance in vitro, comprising
   (a) obtaining a sample of retrovirus-infected cells treated with the substance;
   (b) obtaining a control sample of otherwise identical cells not treated with the substance;
   (c) measuring the levels of Mx proteins in the samples according to the method of claim 3; and
   (d) comparing the levels of Mx proteins in the samples, wherein a decrease in the level of Mx proteins in the treated sample relative to the control indicates that the substance is effective as an antiretroviral agent.

* * * * *